US00PP25673P3

(12) United States Plant Patent
Layt

(10) Patent No.: US PP25,673 P3
(45) Date of Patent: Jul. 7, 2015

(54) ***CALLISTEMON VIMINALIS* PLANT NAMED 'KPS38'**

(50) Latin Name: *Callistemon viminalis*
Varietal Denomination: KPS38

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 155 days.

(21) Appl. No.: 13/986,721

(22) Filed: May 29, 2013

(65) Prior Publication Data

US 2014/0359906 P1 Dec. 4, 2014

(51) Int. Cl.
*A01H 5/00* (2006.01)

(52) U.S. Cl.
USPC ..... Plt./226

(58) Field of Classification Search
USPC ..... Plt./226, 263.1
CPC ..... A01H 5/00; A01H 5/02
See application file for complete search history.

*Primary Examiner* — Kent L Bell
(74) *Attorney, Agent, or Firm* — Samuel R. McCoy, Jr.

(57) ABSTRACT

'KPS38' is a distinctive variety of *Callistemon viminalis* which is characterized by the combination of a compact growth habit and prominent red color of the emerging and immature foliage as well as the stability and uniformity of traits through successive cycles of asexual propagation.

2 Drawing Sheets

Latin name of the genus and species: The Latin name of the genus and species of the novel variety disclosed herein is *Callistemon viminalis*.

Variety denomination: The inventive variety of *Callistemon viminalis* disclosed herein has been given the variety denomination 'KPS38'.

The present application claims priority from a provisional U.S. application Ser. No. 61/656,145 filed Jun. 6, 2012, which is herein incorporated by reference.

BACKGROUND OF THE INVENTION

The present invention relates to a new and distinct perennial variety of *Callistemon viminalis*, which has been given the variety denomination of 'KPS38'. Its market class is that of an ornamental shrub. 'KPS38' is intended for use in landscaping as an accent shrub, hedge, or small tree.

Parentage: The *Callistemon viminalis* variety 'KPS38' was the result of open pollination and was discovered in Clarendon, Sydney, NSW. In 2006 seed was collected from *Callistemon* 'Kings Park Special' (unpatented) plants and many seedlings were grown. Three candidate plants were selected from said seedlings and further grown and evaluated for subsequent testing. In 2009 a final selection took place and one plant was then selected as the final candidate due to the combination of a short height and prominent red color of the emerging and immature foliage. The plant was given the name 'KPS38'.

Asexual Reproduction: 'KPS38' was first asexually propagated by softwood cuttings in 2009 at a commercial plant breeding facility in Clarendon, New South Wales, Australia and has since been asexually propagated through four successive generations. The distinctive characteristics of the inventive 'KPS38' variety are stable from generation to generation; plants of the variety produced by asexual reproduction maintain the distinguishing characteristics of the original plant.

SUMMARY OF THE INVENTION

'KPS38' is a distinctive variety of *Callistemon viminalis* which is characterized by the combination of a compact growth habit and prominent red color of the emerging and immature foliage.

BOTANICAL DESCRIPTION OF THE PLANT

Figure 1:
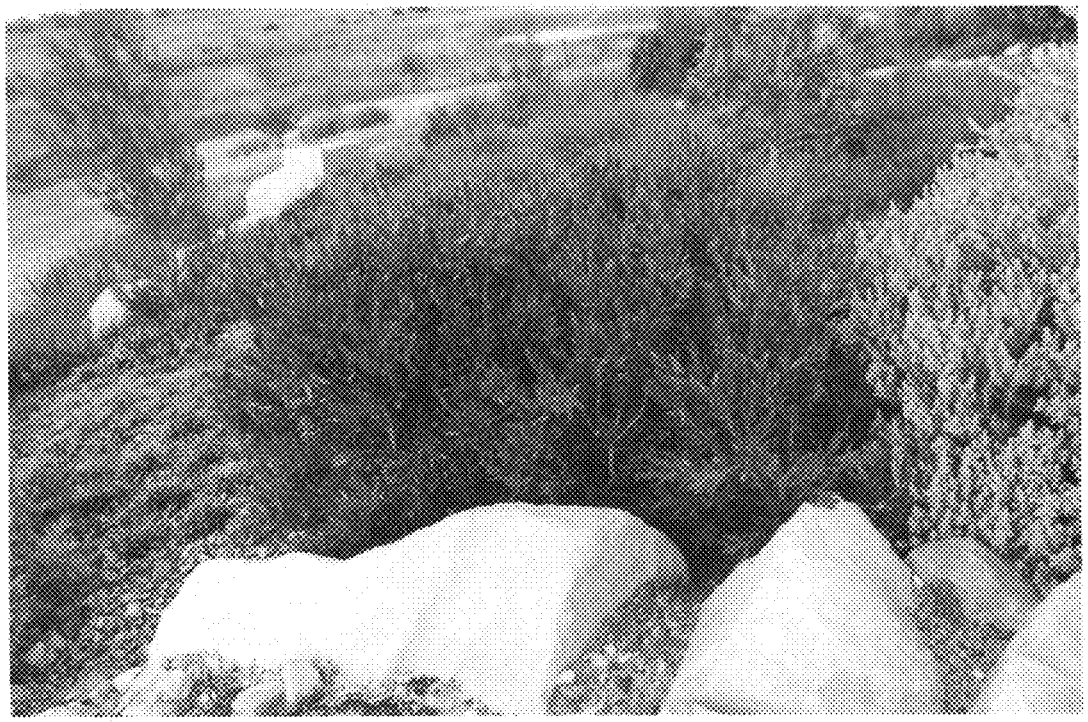
FIG. 1 shows several representative 'KPS38' plants, in the ground, at approximately 3 years old. Of note is the prominent red emerging and immature foliage.
Figure 2:
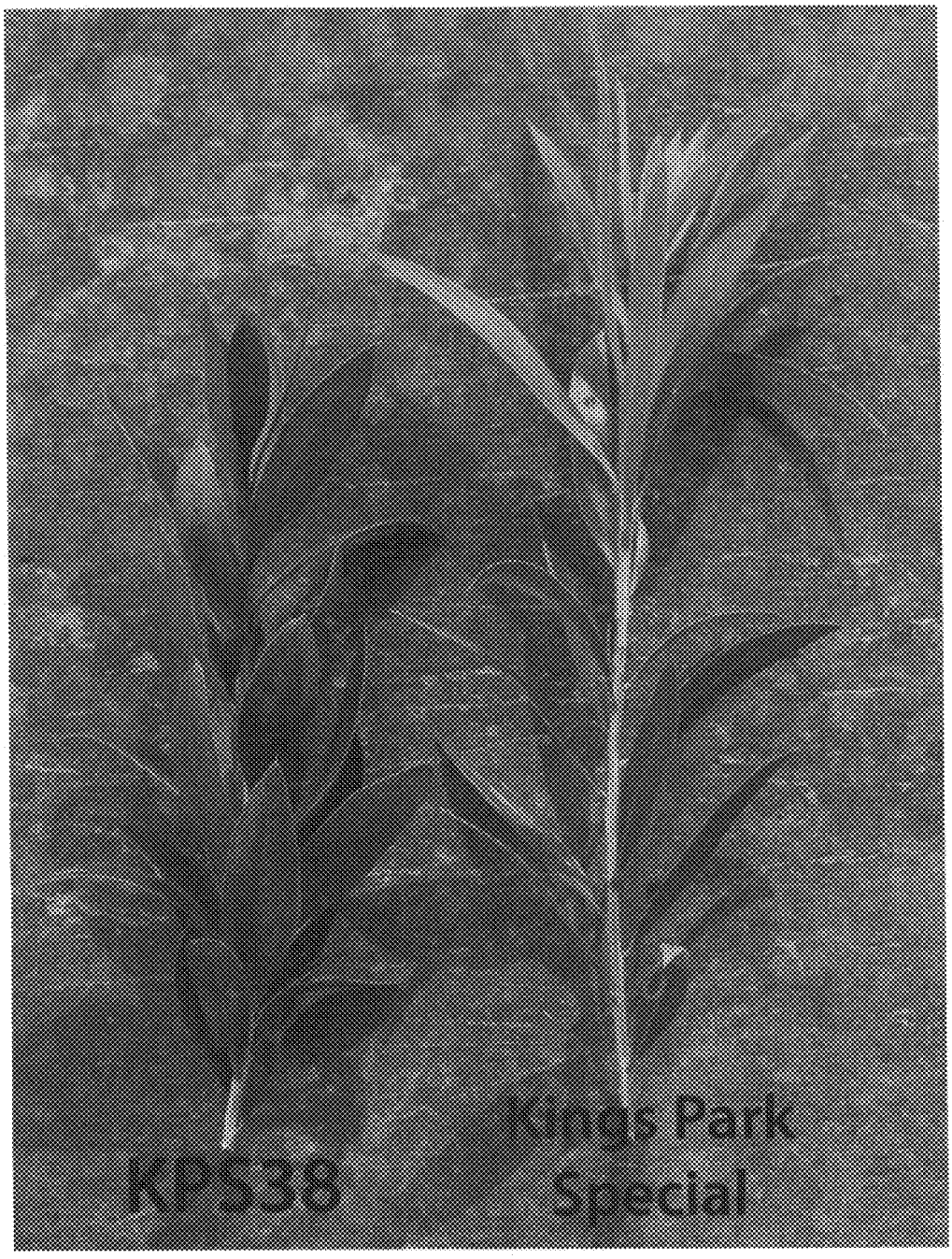
FIG. 2 shows the prominent red coloration of the immature foliage of 'KPS38' compared to that of seed parent 'Kings Park Special'. Also of note is the difference in foliage dimensions, texture and shorter internode length of 'KPS38'.

The following is a detailed botanical description of a new and distinct variety of *Callistemon viminalis* known as 'KPS38' based upon observations of 24-month old plants grown from rooted cuttings into 400 mm nursery pots in full sun in open beds in Clarendon, New South Wales, Australia during spring 2011 until autumn of 2012. Unless indicated otherwise, the descriptions disclosed herein are based upon observations made from mature 'KPS38' plants grown in full sun from rooted cuttings filled with soilless potting media, maintained with granular slow release fertilizer, and regularly watered with overhead irrigation. No pest and disease measures were taken. Observation data was recorded in May of 2012.

Those skilled in the art will appreciate that certain characteristics will vary with older or, conversely, with younger plants. 'KPS38' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2001 edition.

A botanical description of 'KPS38' and comparisons with other varieties of *Callistemon viminalis* are provided below.

TECHNICAL DESCRIPTION OF THE VARIETY

Plant description:

*Plant habit*.—Shrub; upright, rounded and dense.

*Height*.—Approximately 2.0 to 2.4 m.

*Width*.—Approximately 1.5 to 2.0 m.

*Bloom period*.—Bloom not yet observed.

*Hardiness*.—USDA Zone 8 to 11.

*Environmental tolerances*.—Similar to the parent plant; tolerates light shade, a wide range of soil conditions and drought tolerant once established.

*Pest and disease susceptibility or resistance*.—In common with the species, none of note.

*Propagation*.—Propagation is accomplished using softwood cuttings and roots well without the aid of rooting compound or hormone. Time to develop roots is approximately 2 to 4 weeks and an average crop time is approximately 12 months to produce a mature and marketable 400 mm container, starting from a rooted cutting.

Stem:

*Branching and habit*.—Degree of branching is considered medium to strong relative to the UPOV standard of *Callistemon* branching; branch angles acute, branch attitude is erect to semi erect.

*Stem strength*.—Woody and strong.

*Shape*.—Cylindrical.

*Stem color*.—Immature stem is closest to greyed orange RHS 168D. Mature basal stem color is closest to grey brown RHS 199D.

*Stem dimensions*.—Basal stems reach approximately 32 to 37 cm in length before branching; diameter is approximately 12 mm near the base and 2 mm near apex.

*Stem surface*.—Corky, smooth. Immature stems are lightly pubescent while mature stems are glabrous.

*Internode length*.—Ranges from 20 to 25 mm.

Foliage:

*Type*.—Evergreen.

*Shape*.—Elliptical.

*Division*.—Simple.

*Apex*.—Mucronate.

*Base*.—Cunneate.

*Venation*.—Pinnate.

*Vein color* (*adaxial surfaces*).—147A.

*Vein color* (*abaxial surfaces*).—147A.

*Margins*.—Mature margin is entire; immature margin is ciliate.

*Arrangement*.—Alternate.

*Attachment*.—Petiolate.

*Texture*.—Leathery.

*Surfaces* (*adaxial surface*).—Juvenile: medium pubescence; mature: glabrous.

*Surfaces* (*abaxial surface*).—Juvenile: medium pubescence; mature: glabrous.

*Mature leaf dimensions*.—Average length is 52 mm and the average width is 12.3 mm with a length-to-width ratio of 4.2:1.

*Leaf color* (*adaxial surface*).—Juvenile: is red 181B; mature: 147A.

*Leaf color* (*abaxial surface*).—Juvenile: is red 181B; mature: 147A.

*Petiole*.—Approximately 1 mm in length. Red 181B in color.

*Stipules*.—None observed.

Inflorescence:

*Inflorescence*.—To date, 'KPS38' has not bloomed.

*Flowers*.—Not applicable.

*Bud*.—Not applicable.

Reproductive organs: Not applicable.

Fruit and seed production: Not applicable.

COMPARISONS WITH OTHER *CALLISTEMON*

When compared with seed parent *Callistemon viminalis* 'Kings Park Special' (unpatented), 'KPS38' is distinguished by a short height, short leaf length and vivid red color of immature foliage. There are two commercially available cultivars, known to the breeder, which are reported to have similar attributes to those that distinguish 'KPS38' as a novel variety: *Callistemon salignus* 'Great Balls of Fire' (unpatented) and *Callistemon viminalis* 'CC19' (U.S. Provisional Patent Application No. 69/569,988).

When compared with 'Kings Park Special', 'KPS38' has a plant height of approximately 2 to 2.4 m whereas 'Kings Park Special' is significantly taller at approximately 5 m once mature. The foliage characteristics of 'Kings Park Special' and 'KPS38' are different in several regards. 'KPS38' has an elliptical leaf shape with foliage dimensions of 52 mm long by 12.3 mm wide (averages) and a length-to-width ratio of 4.2:1 whereas 'Kings Park Special' has a lanceolate leaf shape with dimensions of 70 mm long and 10 mm wide and a length-to-width ratio of 7.1:1. The mature foliage of both 'KPS38' and 'Kings Park Special' are yellow green 147A however the immature foliage of 'KPS38' is red 181B in color whereas the immature foliage color of 'Kings Park Special' is a maroon color corresponding to N199A.

By comparison with 'Great Balls of Fire', 'KPS38' has a medium plant height of 2.0 to 2.4 m whereas 'Great Balls of Fire' has a mature plant height of 1.5 to 1.75 m. Both 'Great Balls of Fire' and 'KPS38' have a higher expression of anthocyanin in emerging and immature foliage by comparison to their respective seed parents. However the emerging and immature foliage of 'KPS38' is red 181B whereas 'Great Balls of Fire' is greyed purple (183C RHS 1986).

'CC19' is similar to 'KPS38' in that the emerging and immature foliage of 'CC19' also has an above normal expression of anthocyanin. However, in 'KPS38' this higher level of anthocyanin is expressed as red 181B whereas in 'CC19' the emerging and immature foliage varies from greyed orange 167B to greyed orange 174A. The foliage dimensions of the two varieties are also worthy of note. The foliage of 'KPS38' has an average length of 52 mm and an average width of 12.3 mm (length-to-width ratio of 4.2:1) whereas 'CC19' has an average length 59.2 mm and an average width 6.6 mm (length-to-width ratio of 9.0:1). The mature plant heights of 'CC19' and 'KPS38' are also significantly different. 'KPS38' has a mature height of 2.0 to 2.4 m whereas 'CC19' has a mature height of 1.0 to 1.5 m.

That which is claimed is:

1. A new and distinct variety of *Callistemon viminalis* plant named 'KPS38', substantially as described and illustrated herein.

* * * * *